US010473653B2

(12) United States Patent
Tran et al.

(10) Patent No.: US 10,473,653 B2
(45) Date of Patent: Nov. 12, 2019

(54) METHOD FOR QUANTIFYING AN ANALYTE, AND AN AUTOMATIC ANALYTICAL DEVICE CONFIGURED TO IMPLEMENT SAID METHOD

(71) Applicant: Immunodiagnostic Systems Limited, Tyne & Wear (GB)

(72) Inventors: Jacqueline Tran, Westminster, CA (US); Norbert Brutt, Beurey Bauguay (FR); Loic Cornaut, Fontaine les Dijon (FR)

(73) Assignee: IMMUNODIAGNOSTIC SYSTEMS LIMITED, Tyne & Wear (GB)

( * ) Notice: Subject to any disclaimer, the term of this patent is extended or adjusted under 35 U.S.C. 154(b) by 501 days.

(21) Appl. No.: 15/101,411

(22) PCT Filed: Dec. 3, 2014

(86) PCT No.: PCT/EP2014/076367
§ 371 (c)(1),
(2) Date: Jun. 2, 2016

(87) PCT Pub. No.: WO2015/082526
PCT Pub. Date: Jun. 11, 2015

(65) Prior Publication Data
US 2016/0313315 A1 Oct. 27, 2016

(30) Foreign Application Priority Data
Dec. 3, 2013 (EP) .................................... 13195534

(51) Int. Cl.
| | | |
|---|---|---|
| *G01N 33/53* | (2006.01) | |
| *G01N 33/543* | (2006.01) | |
| *G01N 33/74* | (2006.01) | |
| *G01N 33/82* | (2006.01) | |
| *G01N 33/92* | (2006.01) | |
| *G01N 35/00* | (2006.01) | |
| *G01N 35/02* | (2006.01) | |
| *G01N 35/04* | (2006.01) | |

(52) U.S. Cl.
CPC . *G01N 33/54333* (2013.01); *G01N 33/54326* (2013.01); *G01N 33/743* (2013.01); *G01N 33/82* (2013.01); *G01N 33/92* (2013.01); *G01N 35/0098* (2013.01); *G01N 35/025* (2013.01); *G01N 2035/0446* (2013.01); *G01N 2035/0465* (2013.01)

(58) Field of Classification Search
None
See application file for complete search history.

(56) References Cited

U.S. PATENT DOCUMENTS

| | | | | |
|---|---|---|---|---|
| 5,242,833 A | * | 9/1993 | Lawlor | G01N 33/54326 210/222 |
| 5,310,688 A | * | 5/1994 | Zale | B01D 15/3809 210/500.21 |
| 2003/0109618 A1 | * | 6/2003 | Parker | B03C 1/01 524/431 |
| 2009/0117620 A1 | | 5/2009 | Fritchie et al. | |
| 2009/0211979 A1 | * | 8/2009 | Srinivasan | G01N 30/96 210/656 |
| 2010/0068725 A1 | * | 3/2010 | Armbruster | G01N 33/82 435/7.1 |
| 2011/0300621 A1 | * | 12/2011 | Belz | B01L 9/543 435/287.2 |

FOREIGN PATENT DOCUMENTS

CN 101639478 A 2/2010

OTHER PUBLICATIONS

Fraser et al., Measurement of plasma 1,25 dihydroxyvitamin D using a novel immunoextraction technique and immunoassay with iodine labelled vitamin D tracer, Ann Clin Biochem 1997, 34, pp. 632-637. (Year: 1997).*
Amita Rastogi et al. "Immunomagnetic Separation of Subpopulations of Apolipoprotein A-I", Mayo Clinic Proceedings, Jan. 1, 1994, vol. 69, No. 2, pp. 137-143.
B. H. Welter et al. "Magnetic Separation to Concentrate the Estrogen Receptor From Adipose Tissue for Western Analysis", Biotechniques, Informa Healthcare, Aug. 1, 1999, vol. 27, No. 2, pp. 282-286.
International Search Report dated Jan. 21, 2015 re: Application No. PCT/EP2014/076367, pp. 1-5, citing: Ulrich et al., CN 101 639 478 A, Welter et al., Sexton et al., Zhao et al., Xin et al. "Determination", Xin et al. "Development . . . ", Rastogi et a.
Lixie Zhao et al. "Development of a miro-plate magnetic chemiluminescence enzyme immunoassay (MMCLEIA) for rapid- and high-throughput analysis of 17beta-estradiol in water samples", Journal of Biotechnology, Aug. 4, 2005, vol. 118, No. 2, pp. 177-186.
Patricia S Sexton et al. "Immunomagnetic capture of lens membrane fractions containing steriod binding protein, Biochemical and Biophysical Research Communications", Jul. 1, 2002, vol. 295, No. 4, pp. 1027-1031.

(Continued)

*Primary Examiner* — Gary Counts
(74) *Attorney, Agent, or Firm* — Cantor Colburn LLP

(57) ABSTRACT

A novel method for determining the amount of an analyte in a sample comprising an initial purification step, occurring in a first container, comprising the following steps of mixing the sample, a delipidation agent and magnetic particles coated with first analyte binding partners in the first container, incubating the mix, removing the unbound reagents from the mix, and eluting the bound analyte in an elution solution; a transferring step consisting transferring in a volume of the elution solution comprising the analyte from the first container to a second container; and a quantification step, occurring in the second container, consisting of quantifying the analyte in said elution solution.

18 Claims, 3 Drawing Sheets

(56) References Cited

OTHER PUBLICATIONS

Tian-Bing Xin et al. "Development of Magnetic Particle-based Chemiluminescence Enzyme Immunoassay for the Detection of 17[beta]-estradiol in Environmental Water", Applied Biochemistry and Biotechnology, Oct. 8, 2008, vol. 158, No. 3, pp. 582-594.
Tian-Bing Xin et al. "Determination of estradiol in human serum using magnetic particles-based chemiluminescence immunoassay", Analytica Chimica ACTA, Oct. 10, 2008, vol. 627, No. 2, pp. 277-284.
Ulrich Reidt et al. "Automated Immunomagnetic Processing and Separation of With Manual Detection by Sandwich ELISA and PCR Amplification of the ompS Gene", Journal of Laboratory Automation, Apr. 1, 2011, vol. 16, No. 2, pp. 157-164.
Written Opinion dated Jan. 21, 2015 re: Application No. PCT/EP2014/076367, pp. 1-7, citing: Ulrich et al., CN 101 639 478 A, Welter et al., Sexton et al., Zhao et al., Xin et al. "Determination", Xin et al. "Development . . . ".

* cited by examiner

METHOD FOR QUANTIFYING AN ANALYTE, AND AN AUTOMATIC ANALYTICAL DEVICE CONFIGURED TO IMPLEMENT SAID METHOD

FIELD OF INVENTION

The present invention relates to a novel method for determining the amount of an analyte in a sample, and more particularly to a method employing immunoassays, and an automatic analytical device configured to implement said method.

BACKGROUND

The present invention relates to a method for quantifying the amount of an analyte present in a sample and in particular to a method which enable the quantification of an analyte without the need for a prior complex and laborious pre-analytical phase of sample purification.

The present invention also relates to methods for determining the amount of an analyte for use in the diagnosis of a disease.

Simplification of the methods for extraction and separation has been a key feature in improvement of methods. The requirement for a separate purification step notably lengthens the method time and introduces potential error either in the concentration determination but also in the tracability of the samples due to at least one step of manual manipulation of the samples.

The removal of compounds such as lipid from a sample often requires a precipitation step which necessitates a number of manual manipulations and centrifugations. One of the analyte purification steps prior to quantification may require the use of organic solvents, which can be toxic and may need evaporation equipment which is not convenient for use in clinical biochemical laboratories.

DESCRIPTION OF THE INVENTION

The present invention aims to overcome the problems associated with the prior existing method.

Thus the present invention satisfies the need for a simple yet effective method for quantifying an analyte in a sample. It is based on the elimination of the complex manual operation of delipidation-extraction-purification. The invention has enabled a method which reduces considerably the turn-around time, which is more efficient than previous methods and thus more cost-effective, allows full traceability of all operations and therefore better adapted for routine use in clinical laboratories.

The invention is based on the discovery that one-step purification (where sample, delipidation agent and analyte binding partner are mixed in the same container) works efficiently.

As such, in a first aspect, the invention relates to a method for quantifying an analyte in a sample, comprising:
an initial purification step, occurring in a first container, comprising the following steps:
  a) mixing the sample, a delipidation agent and first magnetic particles coated with first analyte binding partners in the first container,
  b) incubating the mix contained in the first container so as to precipitate lipids contained in the sample and bind the analyte contained in the sample to the first analyte binding partners,
  c) subjecting the first container to a magnetic field so as to magnetically attracting the first magnetic particles to an inner wall portion of the first container,
  d) removing unbound reagents from the mix contained in the first container,
  e) eluting the bound analyte in an elution solution so as to separate the analyte from the first analyte binding partners,
a transferring step comprising the following steps:
  f) subjecting the first container to a magnetic field so as to magnetically attracting the first magnetic particles to an inner wall portion of the first container,
  g) transferring a volume of the elution solution comprising the analyte from the first container to a second container, and
a quantification step, occurring in the second container, consisting of the quantification of the analyte in said elution solution.

The present invention may be performed on any human aqueous biological medium such as blood, serum or plasma.

According to an aspect of the invention, at least one of the first and second containers is a cuvette, a tube or a similar recipient. Each of the first and second containers may be a cuvette, a tube or a similar recipient.

According to an aspect of the invention, at least one of the first and second containers is made by glass or plastic. Each of the first and second containers may be made by glass or plastic.

Said transferring step can be done using means a sampling and pipetting device.

According to an aspect of the invention, the incubating step comprises a step of delipidation of the sample.

It should be noted that the delipidation agent is advantageously configured to favour the precipitation of lipids contained in the sample.

The delipidation agent may be a polyanionic analyte such as dextran sulphate, phophotungstic acid or heparin in the presence of Group II cation such as magnesium, manganese or calcium.

This incubation with the delipidation agent allows the lipids to precipitate (thanks to the delipidation agent) and the analyte to bind to the first analyte binding partners coated on the magnetic particles.

According to an aspect of the invention, the removing step comprises a washing step consisting in washing the first magnetic particles with a washing solution.

In a specific aspect of the invention, the elution solution results from the addition of a basic solution such as NaOH, for example 0.3 N to 0.6 N NaOH into the first container comprising the bound analyte. Then a neutralization solution, such as citric acid, more particularly 0.3 to 0.6 M citric acid, and a method buffer are added into the first container.

In an even more specific aspect of the invention, the method buffer comprises BSA, polypep, manitol, sucrose, triton-antioxidant mixture, sodium ascorbate, trolox, and sodium hydrogen carbonate in MOPS buffer.

According to an aspect of the invention, addition and removal of any liquid (reagent in solution, buffer, washing solution, etc.) into or from the first and second containers can be done using pipetting means.

According to an aspect of the invention, the analyte can be any vitamin D metabolite, more preferably 1.25-dihydroxy vitamin D (1.25D), or steroids such as aldosterone, androgens, estrogens, progestogens, or cholesterol. The vitamin D metabolite may also be 25-hydroxy vitamin D, such as 25-hydroxy vitamin $D_2$ or 25-hydroxy vitamin $D_3$.

According to a preferred aspect of the invention, the analyte is the 1,25-dihydroxy Vitamin D (1,25D). This analyte is in very low concentration in the blood and its measurement is challenging as the normal concentration varies from 10 to 100 picogrammes/ml.

The concentration of 1,25D in human blood serves as an excellent indicator of the effectiveness of vitamin D metabolism in the body and is a good indicator of chronic kidney disease.

Development of methods for determining levels of 1,25D has been difficult, mainly due to the extremely low concentrations of 1,25D in blood fluids.

The measurement of 1,25D is known for its labour intensive multiple extraction steps prior to analysis on an automated system or using a manual method. Existing extraction methods available in the market today require a large amount of equipment including purification columns, rotator, centrifuge, and nitrogen evaporator. Solvent is often needed. Positive identification of samples is compromised.

The quantification of the analyte can be performed by any technology well known to the skilled man in the art. The present invention relates, in general, to the following technologies for performing the quantification of the analyte:
- clinical chemistry or biochemistry tests that are carried out using blood serum or other aqueous biological media and in which the principle of measurement used is essentially spectrophotometry;
- immunoassays carried out according to different technical methods such as ELISA, EIA, the measurement being carried out by spectrophotometry, fluorescence or CLIA by luminescence.

In a specific aspect of the invention, the quantification of the analyte is performed by immunoassay, said immunoassay being performed using a second analyte binding partner.

In a specific aspect of the invention, at least one of the first and second analyte binding partners, and for example each of said first and second analyte binding partners, can be a polyclonal, monoclonal, chimeric, engineered or humanized antibody, a scFV or a Fab fragment.

In a specific aspect of the invention, the first and second analyte binding partners are either identical or different.

One of the preferred methods for quantifying an analyte present in a sample at low concentrations is by way of a competitive binding method. This competitive binding method is required when the analyte is a small molecule and does not offer multiple binding possibilities. Suitable competitive binding methods take various forms, and will be well known to persons skilled in the art. A typical competitive binding method will involve bringing analyte binding partners into contact with a labeled form of an analyte and a sample suspected of containing an unlabelled form of the same analyte.

The amount of labelled analyte which is found bound to the analyte binding partners is indicative of the proportion of unlabeled analyte in the sample. Alternatively, the competitive binding method may involve providing analyte binding partners bound to a labeled form of the analyte, adding to the analyte binding partners the sample suspected of containing the unlabelled form of the analyte, and measuring the amount of displaced labelled analyte which is indicative of the amount of unlabelled analyte present.

In a more specific and preferred aspect, the method of the invention can be done in a fully automated way. According to an even more preferred aspect of the invention, the method is performed by an automatic analytical device, such as an automatic immunoassay analyzer.

The innovation inherent in the method is that the preanalytical phase is fully automated on the same instrument instead of being done manually or on a separate equipment.

In an aspect of the invention, all the supplying, pipetting, incubation and mixing steps are managed by the automatic analytical device.

The present invention further relates to an automatic analytical device configured to implement the method according to the present invention, and more particularly to an automatic analytical device including:
- a plurality of containers,
- a rotor having a substantially vertical rotation axis and being rotatably driven about its rotation axis, the rotor delimiting radially outwardly open cavities,
- a loading device suitable for loading containers in the cavities of the rotor,
- at least one sampling and pipetting device suitable for supplying reagents and samples to containers received in cavities of the rotor,
- a magnetic sedimentation and washing module suitable for receiving a container extracted from the rotor and for generating a magnetic field, the magnetic sedimentation and washing module including a pipetting apparatus suitable for pipetting fluids from a container received in the magnetic sedimentation and washing module,
- a magnetic attraction module, also named magnetic separation module, including an upwardly open housing suitable for receiving a container extracted from the rotor, and a first magnetic field generator located nearby the upwardly open housing, and
- a quantification device suitable for receiving a container extracted from the rotor and for quantifying the analyte contained in said extracted container, wherein the sampling and pipetting device is suitable for transferring a volume of solution from a container received in the magnetic attraction module, to an other container received in the rotor.

Thus, once an analyte contained in a first container has been separated from the magnetic particles using the elution solution, the rotor moves the first container into the magnetic attraction module, which attracts the magnetic particles contained in the first container to an inner wall of the latter. Then, the sampling and pipetting device sucks up a certain volume of elution solution in the first container without magnetic particles, and dispenses this volume into a second container received in the rotor.

This second container is used specifically for the quantification of the analyte in the solution. The concentration of the analyte in said elution solution is measured by methods well known to the skilled man in the art, such as a competitive binding method, which is necessary when the molecule of the analyte is small and does not offer multiple binding possibilities. Suitable competitive binding methods take various forms, and will be well known to persons skilled in the art.

In an aspect of the invention, the automatic analytical device comprises a control unit configured to control several devices and modules of the automatic analytical device in order to implement the method according to the invention.

In an aspect of the invention, the first magnetic field generator is located beside the upwardly open housing.

In an aspect of the invention, the first magnetic field generator is configured to extend along a sidewall portion of a container received in the upwardly open housing.

In an aspect of the invention, the first magnetic field generator is configured to attract magnetic particles contained in a container received in the upwardly open housing to an inner wall part of said container, and advantageously to an inner sidewall part of said container.

In an aspect of the invention, the magnetic sedimentation and washing module includes a second magnetic field generator arranged to generate a magnetic field.

In an aspect of the invention, the pipetting apparatus is suitable for supplying a washing solution into a container received in the magnetic sedimentation and washing module.

In an aspect of the invention, the at least one sampling and pipetting device is suitable for supplying a container received in the rotor with a basic solution, and with a method buffer and neutralization solution.

In an aspect of the invention, the at least one sampling and pipetting device is suitable for sucking up a volume of elution solution containing an analyte from a container received in the magnetic attraction module, and for dispensing said volume into an other container received in the rotor.

In an aspect of the invention, the at least one sampling and pipetting device is suitable for sampling samples to be analyzed and reagents from first and second storing zones, and for transferring them into containers located in cavities of the rotor.

In an aspect of the invention, the magnetic attraction module is located above a waste container.

In an aspect of the invention, the upwardly open housing is outwardly and inwardly open, and is particularly radially outwardly and inwardly open.

In an aspect of the invention, the quantification device is configured to measure or determine the amount, such as the concentration, of the analyte contained in the extracted container.

In an aspect of the invention, the quantification device is configured to measure or determine the amount, such as the concentration, of the analyte by binding assay, such as immunoassay or competitive binding assay.

In an aspect of the invention, the quantification device is a luminometer for developing and reading luminescence. The quantification device may include a light proof chamber suitable for receiving a container extracted from the rotor, and a photomultiplier suitable for quantifying a produced luminescence.

BRIEF DESCRIPTION OF THE DRAWINGS

The present invention will now be explained in further details with reference to the accompanying figures, where.

DETAILED DESCRIPTION OF THE INVENTION

Figure 1:
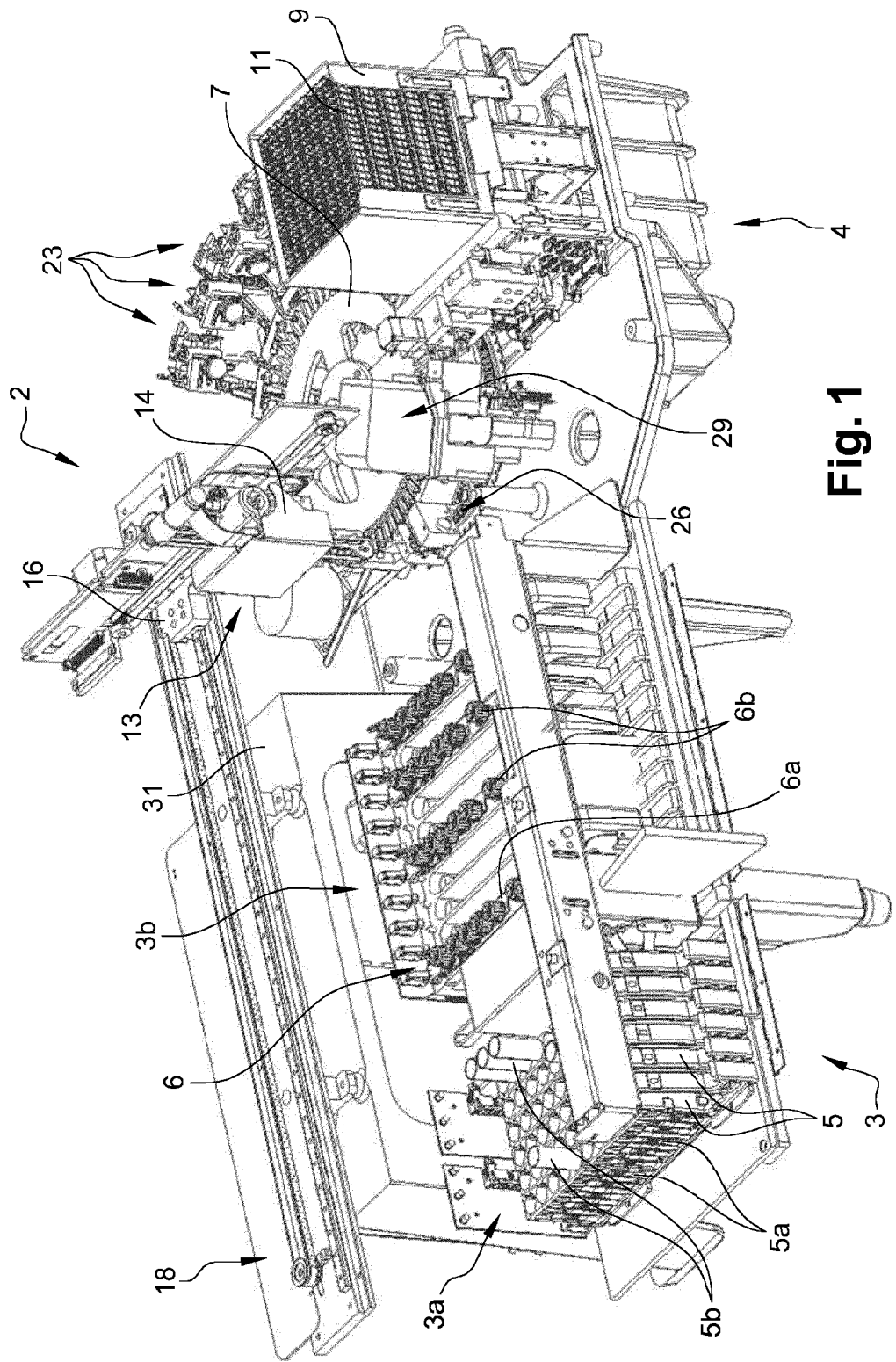
FIG. 1 is a perspective view of an automatic analytical device according to the present invention.
Figure 2:
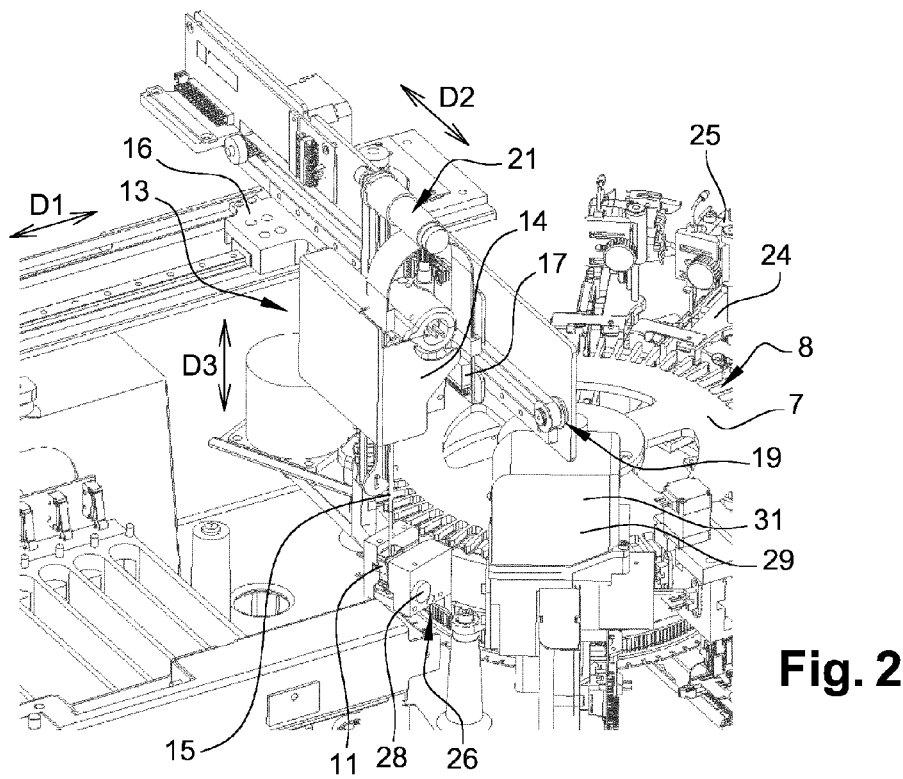
FIG. 2 is a partial perspective view of the automatic analytical device of FIG. 1.
Figure 3:
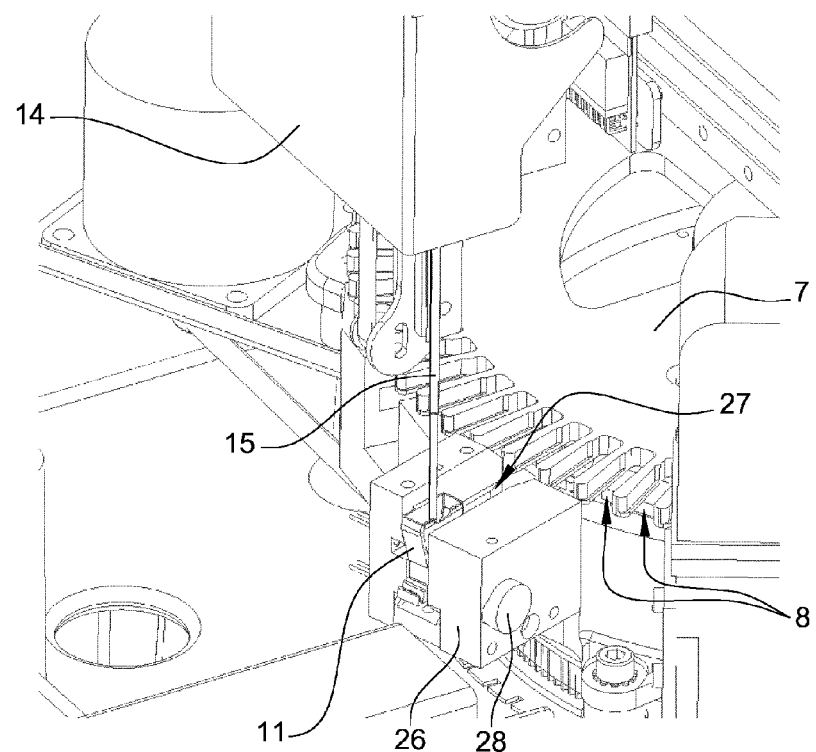
FIG. 3 is a partial perspective view of the automatic analytical device of FIG. 1.

The automatic analytical device 2 for determining the amount of an analyte in a sample according to the present invention is depicted in FIGS. 1 to 3.

The automatic analytical device 2 includes a first part 3 for storing reagents and samples to be analyzed, and a second part 4 for measurement and analysis. The first part 3 comprises a first storage zone 3a suitable for receiving sample cartridges 5 each including a sample carrier 5a and sample receptacles 5b positioned on the sample carrier 5a, and a second storage zone 3b suitable for receiving reagent cartridges 6 each including a reagent carrier 6a and reagent receptacles 6b positioned on the reagent carrier 6a. The samples contained in the sample receptacles may be blood samples, serum or plasma. The reagents contained in the reagent receptacles may be elution solutions, neutralization solutions, buffer solutions, delipidation agents, or solutions containing magnetic particles grafted or coated with analyte binding partners, such as solutions containing magnetic nanoparticles functionalized with antibodies corresponding to the analyte to quantify.

The automatic analytical device 2 further includes a rotor or carousel 7 having a substantially vertical rotation axis and being rotatably driven about its rotation axis by a motor (not shown). The rotor 7 delimits radially outwardly open cavities 8.

The automatic analytical device 2 further includes a loading device 9 suitable for storing reaction cuvettes 11 and for loading said reaction cuvettes 11 in the cavities 8 of the rotor 7.

The automatic analytical device 2 also includes a sampling and pipetting device 13 suitable for sampling samples from the sample cartridges 5 received in the first storage zone 3a, and for sampling reagents from the reagent cartridges 6 received in the second storage zone 3b. The sampling and pipetting device 13 is also suitable for dispensing the sampled samples and reagents in reaction cuvettes 11 received in the cavities 8 of the rotor 7.

Particularly, the sampling and pipetting device 13 includes a sampling head 14 having a sampling needle 15. The sampling and pipetting device 13 further includes a first support member 16 displaceable along a first horizontal direction D1 with respect to the casing of the automatic analytical device 2, and a second support member 17 supported by the first support member 16 and displaceable with respect to the first support member 16 along a second horizontal direction D2 orthogonal to the first horizontal direction D1. The sampling head 14 is supported by the second support member 17 and is displaceable with respect to the second support member 17 along a vertical direction D3.

The sampling and pipetting device 13 further includes first displacing means 18 suitable for displacing the first support member 16 along the first horizontal direction D1, second displacing means 19 suitable for displacing the second support member 17 along the second horizontal direction D2, and third displacing means 21 suitable for displacing the sampling head 14 along the vertical direction D3.

Advantageously, the sampling head 14 is suitable to oscillate the sampling needle 15. This provision allows to mix the content of a reaction cuvette 11 when the sampling needle 15 is located in the latter.

The automatic analytical device 2 further includes at least one or a plurality of magnetic sedimentation and washing modules 23 radially oriented with respect to the rotor 7. Each magnetic sedimentation and washing module 23 includes a sedimentation part 24 having a magnetic field generator, such as a permanent magnet or an electromagnet, arranged to generate a magnetic field, and a pipetting apparatus 25 arranged for removing liquid content from a reaction cuvette 11 positioned in the sedimentation part 24 and for introducing a washing solution into said reaction cuvette 11.

The automatic analytical device 2 also includes first linear actuators (not shown) each associated to a magnetic sedimentation and washing module 23. Each first linear actuator is suitable for extracting a reaction cuvette 11 from the rotor 7 in a centrifugal radial movement and for positioning the extracted reaction cuvette 11 nearby the magnetic field generator of the corresponding magnetic sedimentation and washing module 23.

Thus, when a reaction cuvette 11 containing magnetic particles coated with analyte binding partners is positioned in a magnetic sedimentation and washing station 23, the corresponding magnetic field generator attracts the magnetic particles contained in said reaction cuvette 11 to an inner wall part of the latter, and the content of the reaction cuvette 11, except the magnetic particles and the analyte bound to said magnetic particles, is suctioned out by the pipetting apparatus 25 of said magnetic sedimentation and washing station 23. Then a washing solution is introduced into the reaction cuvette 11 by the pipetting apparatus 25 in order to wash the magnetic particles. After a predetermined time, said washing solution is suctioned out by the pipetting apparatus 25. Once the reaction cuvette 11 has been processed, it is reintroduced onto the rotor 7 by means of a centripetal movement of the first linear actuator associated to said magnetic sedimentation and washing module 23.

The automatic analytical device 2 further includes a magnetic attraction module 26, also named magnetic separation module, radially oriented with respect to the rotor 7 and located nearby the sampling and pipetting device 13. The magnetic attraction module 26 includes a case delimiting an upwardly open housing 27 suitable for receiving a reaction cuvette 11 extracted from the rotor 7, and a magnetic field generator 28, such as a permanent magnet or an electromagnet, mounted on the case and located nearby the upwardly open housing 27. The automatic analytical device 2 includes second linear actuator (not shown) associated to the magnetic attraction module 26, and suitable for extracting a reaction cuvette 11 from the rotor 7 in a centrifugal radial movement and for positioning the extracted reaction cuvette 11 in the upwardly open housing 27, that is nearby the magnetic field generator 28. Advantageously, the upwardly open housing 27 is also radially outwardly and inwardly open.

It should be noted that the sampling and pipetting device 13 is suitable for sampling a volume of the content of a reaction cuvette 11 received in the upwardly open housing 27 of the magnetic attraction module 26, and for dispensing said volume in a reaction cuvette received in the rotor 7.

Thus, when a reaction cuvette 11 containing an elution solution, an analyte and magnetic particles is positioned in the magnetic attraction module 26, the corresponding magnetic field generator 28 attracts the magnetic particles contained in said reaction cuvette 11 to an inner wall portion of the latter, and the content of the reaction cuvette 11, except the magnetic particles, is suctioned out by the sampling and pipetting device 13 and dispensed into an other reaction cuvette 11 received in the rotor 7.

Preferably, the magnetic attraction module 26 is located above a waste container, and is configured such that, when a reaction cuvette 11 is newly introduced in the upwardly open housing 27, said newly introduced reaction cuvette 11 pushes the previously introduced reaction cuvette 11 outside the upwardly open housing 27. Said pushed reaction cuvette 11 then falls by gravity into the waste container.

The automatic analytical device 2 further includes a quantification device 29 suitable for quantifying an analyte contained in a reaction cuvette 11. The quantification device 29 is preferably a luminometer for developing and reading luminescence. The quantification device 29 may notably include a light proof chamber 31 suitable for receiving a reaction cuvette 11 extracted from the rotor 7, and a known photomultiplier (not shown) suitable for quantifying a produced luminescence. This measurement depends on the concentration of the analyte to be measured. Once the measurement is complete, the reaction cuvette 11 is extracted from quantification device 29 and evacuated into the waste container by the action of linear actuators equipping the quantification device 29.

The automatic analytical device 2 also includes a control unit 31 configured to control the above-mentioned devices and modules of the automatic analytical device 2.

The automatic analytical device 2 further includes a rinsing and decontamination system (not shown) suitable for rinsing and decontamination the sampling needle 15 of the sampling and pipetting device 13.

Figure 4:
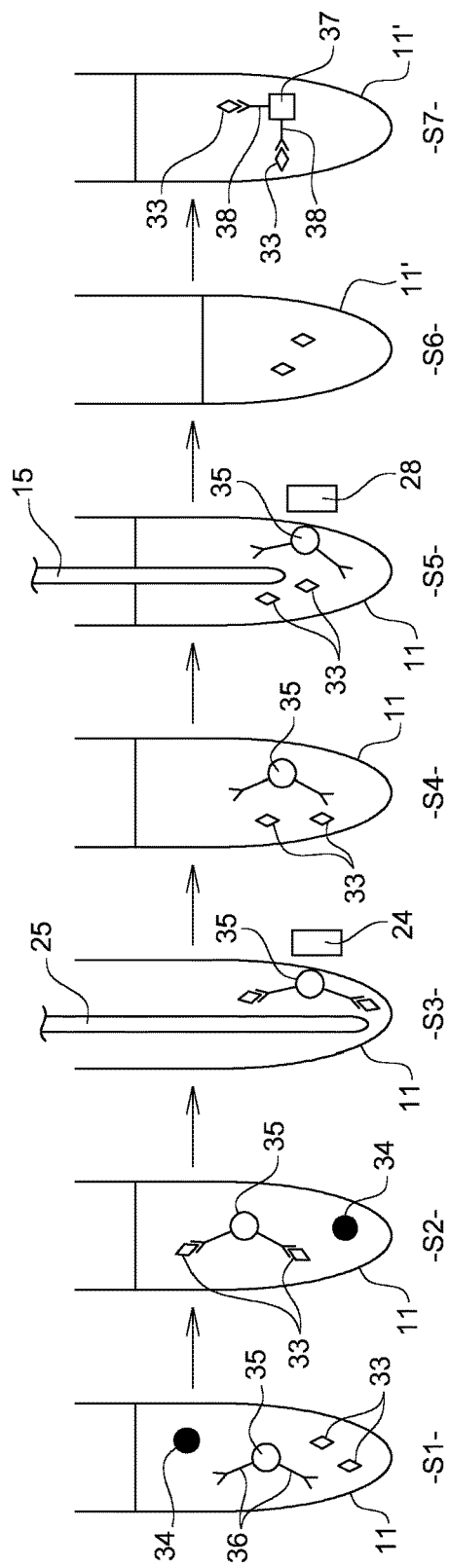
FIG. 4 is a diagram showing a method for determining the amount of an analyte in a sample according to the present invention.

The method for determining the amount of an analyte in a sample according to the present invention is depicted in FIG. 4. Said method is performed by the automatic analytical device 2 according to the present invention.

The method for determining the amount of an analyte in a sample according to the present invention comprises the following steps:

mixing, in a first reaction cuvette 11 received in the rotor 7 and using the sampling and pipetting device 13, the sample containing an analyte 33 to be quantified, a delipidation agent 34, and a first solution containing magnetic particles 35 coated with first analyte binding partners 36 (step S1);

incubating, using the rotor 7, the mix contained in the first reaction cuvette 11 such that the lipids precipitate thanks to the delipidation agent 34 and the analyte 33 binds to the first analyte binding partners 36 (step S2);

transporting, using the rotor 7, the first cuvette 11 in front of a magnetic sedimentation and washing module 23;

extracting the first reaction cuvette 11 from the rotor 7 and positioning said first reaction cuvette 11 nearby the magnetic field generator of said magnetic sedimentation and washing module 23 such that the magnetic field generator thereof attracts the magnetic particles 35 to an inner wall part of the first reaction cuvette 11;

sucking up the unbound reagents from the first cuvette 11 using the pipetting apparatus 25 of the magnetic sedimentation and washing module 23 (step S3);

dispensing a washing solution into the first cuvette 11 using the pipetting apparatus 25 in order to wash the magnetic particles;

sucking up the washing solution from the first cuvette 11 using the pipetting apparatus 25;

reloading the first reaction cuvette 11 that has been washed in the rotor 7;

supplying an elution solution into the first reaction cuvette 11, using the sampling and pipetting device 13, so as to elute the bound analyte, i.e. separate the analyte 33 from the magnetic particles 35 (step S4);

transporting the first cuvette 11 in front of the magnetic attraction module 26, using the rotor 7;

extracting the first reaction cuvette 11 from the rotor 7 and positioning the first cuvette 11 in the magnetic attraction module 26 such that the magnetic field generator 28 thereof attracts the magnetic particles 35 to an inner wall part of the first reaction cuvette 11;

sucking up, using the sampling and pipetting device 13, the elution solution and the analyte from the first reaction cuvette 11 (step S5);

dispensing, using the sampling and pipetting device 13, the elution solution and the analyte 33 to a second empty reaction cuvette 11' received in the rotor 7 (step S6);

supplying the second reaction cuvette 11' with a second solution containing magnetic particles 37 coated with second analyte binding partners 38, using the sampling and pipetting device 13 (step S7); and quantifying the analyte in the elution solution contained in the second reaction cuvette 11'.

The invention will be illustrated with reference to the following examples, all not limited and non-exhaustive:

EXAMPLES

Example 1

Measurement of the Amount of 1.25D Concentration in a Sample According to the Invention The assay of 1,25D in human blood serves as an excellent indicator of the effectiveness of vitamin D metabolism in the body.

Development of assay methods for determining levels of 1,25D has been difficult, mainly due to the extremely low concentrations of 1,25D in blood fluids.

1,25D is well-known for its labour intensive multiple extraction steps prior to analysis on an automated system or using a manual method. Existing extraction methods available in the market today require a large amount of equipment including purification columns, rotator, centrifuge, and nitrogen evaporator. Solvent is often needed. Positive identification of samples is compromised.

Measurement of 1,25D in a sample according to the invention is started with sample pre-treatment for 1,25D in a first cuvette with sample delipidation. Delipidation is done with 22 µL of 10 g dextran sulphate (50 k), Sigma catalogue number D8787, in one liter of 0.5M magnesium chloride and 218 µL sample.

Immediately afterwards 1,25D is captured onto 46 µL anti-1,25D antibody coated magnetic particles (MP) in conjunction with 314 µL optimized displacer solution. Displacer reagent is composed of 4.035 g potassium phosphate dibasic trihydrate, 0.489 g potassium phosphate monobasic, 19.5 g sodium chloride, 4.19 g ANSA, 0.209 g warfarin, and 104.7 mL methanol in 1 liter.

The anti-1,25D coated MP is made by coupling anti-1, 25D antibody at 36-144 mg antibody per 1 g Sera-Mag® Speedbeads carboxylate-modified particle. The MP diameter is 0.8 µm obtained from Thermo Scientific catalogue number 45152105050350. Ten minute incubation of delipidated sample with MP at 37° C. was found to be sufficient to capture 1,25D onto particles.

Wash MP with wash solution comprised of 0.6 g potassium phosphate dibasic trihydrate, 0.97 g potassium phosphate monobasic, 1.0 g sodium chloride, 1.0 g TWEEN® 20, 1.0 g proclin-300, and 0.1 g sodium azide in 1 liter water (IDS catalogue number IS-CW100). At least 4 separate washes of MP is needed followed by 1 wash of MOPS buffer, comprised of 231 mg MOPS sodium salt, 209 mg MOPS, and 0.9 g sodium azide, to remove unbound and precipitate in the reaction mixture.

Elute captured 1,25D on MP with 75 µl of 0.4N sodium hydroxide for 6 minutes. A neutralisation step follows with 25 µL of 0.4M citric acid and 100 µL of assay buffer to yield the same basic composition as an assay calibrator. 120 µL eluate is transferred from the first cuvette to a second cuvette for 1,25D measurement.

1,25D is measured utilizing 1,25Dihydroxy Vitamin D assay reagent (IDS catalogue number IS-2400). 120 µL eluate containing extracted 1,25D is incubated with the biotinylated sheep anti-1,25D antibody. The 1,25D-Acridinium conjugate is then added, which competes for antibody binding sites. Streptavidin coated magnetic particles are then added and following a further incubation step, the magnetic particles are washed to remove unbound materials. Following the addition of Trigger Reagents, a flash chemiluminescent reaction is initiated. The light signal is measured by the photomultiplier as Relative Light Units (RLU) and is inversely proportional to the amount of 1,25D present in the sample.

The method is able to handle high lipid samples up to 3 g/dL triglycerides, 300 mg/dL cholesterol, and 7.55 g/dL albumin. The fully automated method observed good correlation with the IDS-iSYS 1,25D immunocapsule extraction method in example 2.

The finding here is that it is possible to directly extract 1,25D from human serum with anti-1,25D antibody coated magnetic particles and optimized extraction reagents without having to use multiple items of equipment other than a magnetic separator to wash MP, and collect the eluate from MP. Total extraction process takes about 21 minutes. Time to first result is 93 minutes.

Example 2

Measurement of the Amount of 1.25D Concentration in a Sample According to the Previous Known Method Delipidate sample in a labeled glass or plastic tube by adding 500 µL sample to tube followed by 50 µL delipidation reagent, comprising 10 g dextran sulphate (50 k), Sigma catalogue number D8787, in one liter of 0.5M magnesium chloride. Mix and centrifuge at 2000 g for 15 minutes.

Label capsule. Remove capsule screw cap. Add 150 µL of delipidated sample to a capsule containing a suspension of solid phase to which is attached a monoclonal antibody highly specific for 1,25D. Replace cap securely. The capsule is rotated end-over-end for 90 minutes at room temperature to allow the binding of 1,25D to the monoclonal antibody.

Stand capsule upright for 3-5 minutes allowing gel to settle. Remove screw cap and break off bottom stopper from capsule. Place each capsule in a glass or plastic tube, centrifuge at 500-1000 g for 1 minute.

The capsule is washed 3× with water, 1 minute incubation followed by 1 minute centrifugation at 500-1000 g each time, to remove potential interfering substances.

Transfer capsule to an appropriately labeled 2 mL polypropylene conical skirted base tube. Elute captured 1,25D with 3×150 µL ethanol, 1-2 minutes incubation followed by 1 minute centrifugation at 500-1000 g each time.

Discard capsule. Place micro tube containing eluate in a heating block or water bath to evaporate under gentle flow of nitrogen at 40° C. for 45-60 minutes. Reconstitute each micro tube with 200 µL assay buffer.

The reconstituted immunopurified samples are measured utilizing 1,25Dihydroxy Vitamin D assay reagent (IDS catalogue number IS-2400), as described in example 1.

Total extraction process takes approximately 4 hours. Time to first result is approximately 5 hours.

Of course, the present invention is not restricted to the embodiment described above by way of non-limiting example, but on the contrary it encompasses all embodiments thereof.

The invention claimed is:

1. A method for determining the amount of an analyte in a sample comprising:
   providing an automatic analytical device including:
      a plurality of containers including a first container and a second container,
      a rotor having a substantially vertical rotation axis and being rotatably driven about its rotation axis, the rotor delimiting radially outwardly open cavities,
      a loading device suitable for loading containers of the plurality of containers in the cavities of the rotor,
      at least one sampling and pipetting device suitable for supplying reagents and samples to containers received in cavities of the rotor,
      a magnetic sedimentation and washing module suitable for receiving a container extracted from the rotor and for generating a magnetic field, the magnetic sedimentation and washing module including a pipetting apparatus suitable for pipetting fluids from a container received in the magnetic sedimentation and washing module,
      a magnetic attraction module including an upwardly open housing suitable for receiving a container extracted from the rotor, and a first magnetic field generator located nearby the upwardly open housing, and
      a quantification device suitable for receiving a container extracted from the rotor and for quantifying an analyte contained in said extracted container,
      wherein the sampling and pipetting device is suitable for transferring a volume of solution from a container received in the magnetic attraction module, to an other container received in the rotor,
   a purification step, occurring in the first container, comprising the following steps:
      a) mixing the sample, a delipidation agent and first magnetic particles coated with first analyte binding partners in the first container received in the rotor,
      b) incubating, using the rotor, the mix contained in the first container so as to precipitate lipids contained in the sample and to bind the analyte contained in the sample to the first analyte binding partners,
      c) subjecting the first container to the magnetic field generated by the magnetic sedimentation and washing module so as to magnetically attracting the first magnetic particles to an inner wall portion of the first container,
      d) removing unbound reagents from the mix contained in the first container,
      e) supplying an elution solution into the first container, using the at least one sampling and pipetting device, for eluting the bound analyte so as to separate the analyte from the first analyte binding partners,
   a transferring step comprising the following steps:
      f) subjecting the first container to a magnetic field generated by the magnetic attraction module so as to magnetically attracting the first magnetic particles to an inner wall portion of the first container,
      g) transferring a volume of the elution solution comprising the analyte from the first container to the second container received in the rotor, using the at least one sampling and pipetting device, and
   a quantification step, occurring in the second container, comprising the quantification of the analyte using the quantification device, and
   automatically performing the purification step, the transferring step and the quantification step using the automatic analytical device.

2. The method of claim 1, wherein the analyte is a vitamin D metabolite or a steroid.

3. The method of claim 2, wherein the analyte is 1,25-dihydroxyvitamin D (1.25D) or 25-hydroxy Vitamin D.

4. The method of claim 2, wherein the analyte is a steroid selected from the group consisting of aldosterone, androgens, estrogens, progestogens and cholesterol.

5. The method of claim 1, wherein the sample is an aqueous biological medium.

6. The method of claim 1, wherein the analyte quantification is done using an immunoassay.

7. The method of claim 6, wherein the immunoassay is performed by using second magnetic particles coated with second analyte binding partners.

8. The method of claim 1, wherein each of the first analyte binding partners is a polyclonal, monoclonal, chimeric, engineered or humanized antibody, a scFV or a Fab fragment.

9. The method of claim 1, wherein the delipidation agent is a polyanionic analyte.

10. The method of claim 9, wherein the delipidation agent is a polyanionic analyte selected from the group consisting of dextran sulphate, phophotungstic acid, and heparin in the presence of Group II cation.

11. The method of claim 1, wherein the removing step comprises a washing step comprising washing the first magnetic particles with a washing solution.

12. The method of claim 1, wherein the elution solution is obtained by the addition in the first container of a basic solution followed by addition of a neutralization solution and a method buffer.

13. The method of claim 12, wherein the basic solution is 0.3 N to 0.6 N NaOH.

14. The method of claim 12, wherein the neutralization solution 0.3 to 0.6 M citric acid.

15. The method of claim 12, wherein the method buffer comprises bovine serum albumin, polypep, manitol, sucrose, triton-antioxidant mixture, sodium ascorbate, trolox, and sodium hydrogen carbonate in (3-(N-morpholino)propanesulfonic acid) buffer.

16. The method of claim 1, wherein the purification step, the transferring step and the quantification step are performed by an automatic analytical device.

17. The method of claim 1, wherein the quantification device is configured to measure or determine the amount of the analyte by immunoassay or competitive binding assay.

18. The method of claim 7, wherein each of the second analyte binding partners is a polyclonal, monoclonal, chimeric, engineered or humanized antibody, a scFV or a Fab fragment.

* * * * *